United States Patent [19]
Strauss et al.

[11] Patent Number: 5,932,075
[45] Date of Patent: Aug. 3, 1999

[54] BATCH MICROWAVE REACTOR

[75] Inventors: Christopher Roy Strauss, Richmond; Robert William Trainor, Chadstone; Kevin David Raner, Mount Waverley; John Stanley Thorn, Chatswood, all of Australia

[73] Assignee: Commonwealth Scientific and Industrial Research Organisation, Australia

[21] Appl. No.: 08/624,629

[22] PCT Filed: Oct. 27, 1994

[86] PCT No.: PCT/AU94/00659

§ 371 Date: Jun. 25, 1996

§ 102(e) Date: Jun. 25, 1996

[87] PCT Pub. No.: WO95/11750

PCT Pub. Date: May 4, 1995

[30]    Foreign Application Priority Data

Oct. 28, 1993 [AU] Australia ................................ PM2072

[51] Int. Cl.⁶ ............................. C07C 1/00; B01D 53/00; C07F 1/00; B01J 19/08
[52] U.S. Cl. ................................. 204/157.15; 204/157.3; 204/157.6; 422/186
[58] Field of Search ........................ 204/157.15, 157.43, 204/157.6; 422/186

[56]    References Cited

U.S. PATENT DOCUMENTS

| | | | |
|---|---|---|---|
| 1,191,916 | 7/1916 | Brooks et al. | ........................... 422/186 |
| 1,523,563 | 1/1925 | Snelling | ................................... 422/186 |
| 1,746,731 | 2/1930 | Koehler | ................................... 422/186 |
| 2,958,638 | 11/1960 | Tarnity | .................................... 204/193 |
| 3,458,418 | 7/1969 | Beckmann | ......................... 204/157.15 |
| 4,507,188 | 3/1985 | Chu | .................................... 204/159.23 |
| 5,033,541 | 7/1991 | D'Silva | ................................... 165/155 |

FOREIGN PATENT DOCUMENTS

| | | |
|---|---|---|
| 8944040 | 5/1990 | Australia . |
| 0595084 | 5/1994 | European Pat. Off. . |
| 2281159 | 3/1976 | France . |
| 2140258 | 11/1984 | United Kingdom . |
| 2267845 | 12/1993 | United Kingdom . |

*Primary Examiner*—Kathryn L. Gorgos
*Assistant Examiner*—Edna Wong
*Attorney, Agent, or Firm*—Ladas & Parry

[57]    ABSTRACT

An apparatus for performing batchwise chemical reactions using microwave energy (10-11-12) includes a vessel (15) within a microwave cavity (13). The vessel has a sealed cover (16), located outside cavity (13), which mounts a cold-finger type heat exchanger (24) for immersion in the vessel's contents (23). Cover (16) also mounts a pressure measuring device (17) and a temperature sensing device (20) for monitoring the vessel's contents during a chemical reaction. A pressure operable safety valve (18) and a sampling facility (19) are also mounted on the cover (16). The vessel also contains a magnetically operated stirrer (22). The reactor apparatus is constructed to withstand high pressures and temperatures that may be developed within the vessel (15). Various uses of the cold-finger (24) to facilitate the conduct or completion of a chemical reaction are described.

23 Claims, 4 Drawing Sheets

FIG 4

BATCH MICROWAVE REACTOR

This is a national stage application of PCT/AU94/00659 filed Oct. 27, 1994.

TECHNICAL FIELD

This invention relates to a method and apparatus for performing chemical reactions using microwave energy. The invention is particularly suitable for chemical synthesis or kinetics studies.

In this specification, the term "chemical reaction" means a process involving the making and/or breaking of at least one chemical bond within or between one or more substances so as to produce one or more new substances.

BACKGROUND ART

It is known that the rate of chemical reactions can be accelerated to decrease reaction times by several orders of magnitude by using microwave energy, provided the reaction medium includes at least one solvent or reactant having a high dielectric loss tangent so as to couple effectively with the microwaves. Such accelerated reaction times, however, usually involve the generation of high temperatures and pressures, particularly in sealed reaction vessels, and there exists a need to provide effective reaction monitoring, control and safety facilities on the microwave heating equipment.

The applicant's prior International Application No. PCT/AU89/00437 (Publication No. WO 90/03840) discloses a laboratory flow-through unit for conducting microwave initiated chemical reactions on a continuous basis which incorporates reaction monitoring and control facilities. However, the monitoring and control facilities on this known unit are located outside the microwave irradiation zone. Furthermore, this known unit does not meet laboratory applications that are not suited to continuous processes.

Apparatus for performing chemical reactions on a batch basis that includes facilities to monitor temperature and pressure within the reaction vessel is disclosed by D. Constable, K. Raner, P. Somlo and C. Strauss in the article "A New Microwave Reactor Suitable for Organic Synthesis and Kinetics Studies", Journal of Microwave Power and Electromagnetic Energy, Vol. 27 No. 4, 1992, pages 195–198 (the disclosure of which is incorporated herein by cross-reference). In this reactor, a reaction vessel having a screw-cap lid with pressure and temperature monitoring fittings, is situated within a microwave cavity. The reaction vessel also contains a stirrer bar, which is magnetically driven from outside the microwave cavity.

Although the Constable et al. reactor includes facilities to monitor reaction conditions within the microwave irradiation zone, its only controllable input is the power level of the microwaves. Thus in the Constable et al. reactor it is not possible, for example, to controllably cool the reaction products nor to add or subtract from the vessel's contents during the course of a reaction.

DISCLOSURE OF THE INVENTION

An object of the present invention is to provide a microwave reactor and methods for performing chemical reactions which embody control features additional to those of the Constable et al. reactor.

According to the invention, there is provided a reactor for performing chemical reactions under the influence of microwave radiation comprising a vessel for containing substances for a chemical reaction, said vessel being adapted to withstand internal pressures generated by said substances during the course of a chemical reaction, said adaptation including the provision of a cover containing means for monitoring the vessel contents as microwave energy is applied thereto and wherein the cover also supports a heat exchange means for immersion in the vessel contents.

Preferably the vessel is for placement within a microwave cavity. Alternatively microwave radiation may be introduced interiorly of the vessel by means associated with the cover.

The heat exchange means is for preheating said substances or for cooling said contents when desired, for example during the progress of a chemical reaction, most usually an exothermic reaction, or upon completion of the heating stage for a reaction.

Preferably the means for monitoring the vessel contents comprises temperature and/or pressure measuring means.

The invention in a second aspect provides a method for performing a chemical reaction comprising:

(i) charging a vessel, which is adapted to withstand a high pressure and a high temperature, with at least one reactant or a reactant/solvent mixture, wherein the reactant or solvent or a susceptor mixed therewith is capable of absorbing microwave energy, (ii) applying microwave energy to the vessel sufficient for a chemical reaction to occur, and (iii) rapidly cooling the reaction products while they are still contained in the vessel under pressure via a heat exchange means immersed therein.

The invention also provides, in a third aspect, a method for performing a chemical reaction comprising:

(i) charging a vessel, which is adapted to withstand a high pressure and a high temperature, with at least one reactant or a reactant/solvent mixture which when heated will react exothermically and wherein the reactant or solvent or a susceptor mixed therewith is capable of absorbing microwave energy, (ii) applying microwave energy sufficient for an exothermic chemical reaction to occur, and (iii) during the course of the reaction, cooling the vessel contents while they are contained in the vessel under pressure via a heat exchange means immersed therein.

The susceptor referred to in the above described second and third aspects of the invention may be used when the reaction fluids do not readily absorb microwave energy. That is, the susceptor, being a material that is microwave absorbent, is heated by absorbing microwave energy and transfers its heat to the surrounding reaction fluids by conduction. Suitable susceptors include carbon, magnetite, maghemite and chromium salts.

The invention furthermore provides, in a fourth aspect, a method for performing a chemical reaction comprising:

(i) charging a vessel, which is adapted to withstand a high pressure and a high temperature, with at least one reactant or a reactant/solvent mixture which is a poor absorber of microwave energy at ambient temperature and a good absorber of microwave energy when heated, (ii) immersing a heat exchange means in the vessel contents and sealing the vessel, wherein the heat exchange means is charged with a microwave absorbent medium, (iii) applying microwave energy to the vessel sufficient to heat the medium within the heat exchange means and to thus heat the vessel contents, whereby said contents increasingly absorb microwave energy, (iv) continuing to apply microwave energy to the vessel contents sufficient for a chemical reaction to occur.

Preferably the heat exchange means comprises a cold-finger structure.

The microwave absorbent medium (or susceptor) within the heat exchange means may be, for example, water, dimethylsulfoxide or ethylene glycol or any other suitable medium.

A reactor according to the invention may furthermore include a facility for adding substances to or subtracting them from the reaction vessel during microwave heating. Preferably more than one such facility is provided such that substances can be simultaneously added and subtracted.

BRIEF DESCRIPTION OF THE DRAWINGS

Embodiments of the invention will now be described, by way of example only, with reference to the accompanying drawings in which.

BEST MODE FOR CARRYING OUT THE INVENTION

Figure 1:
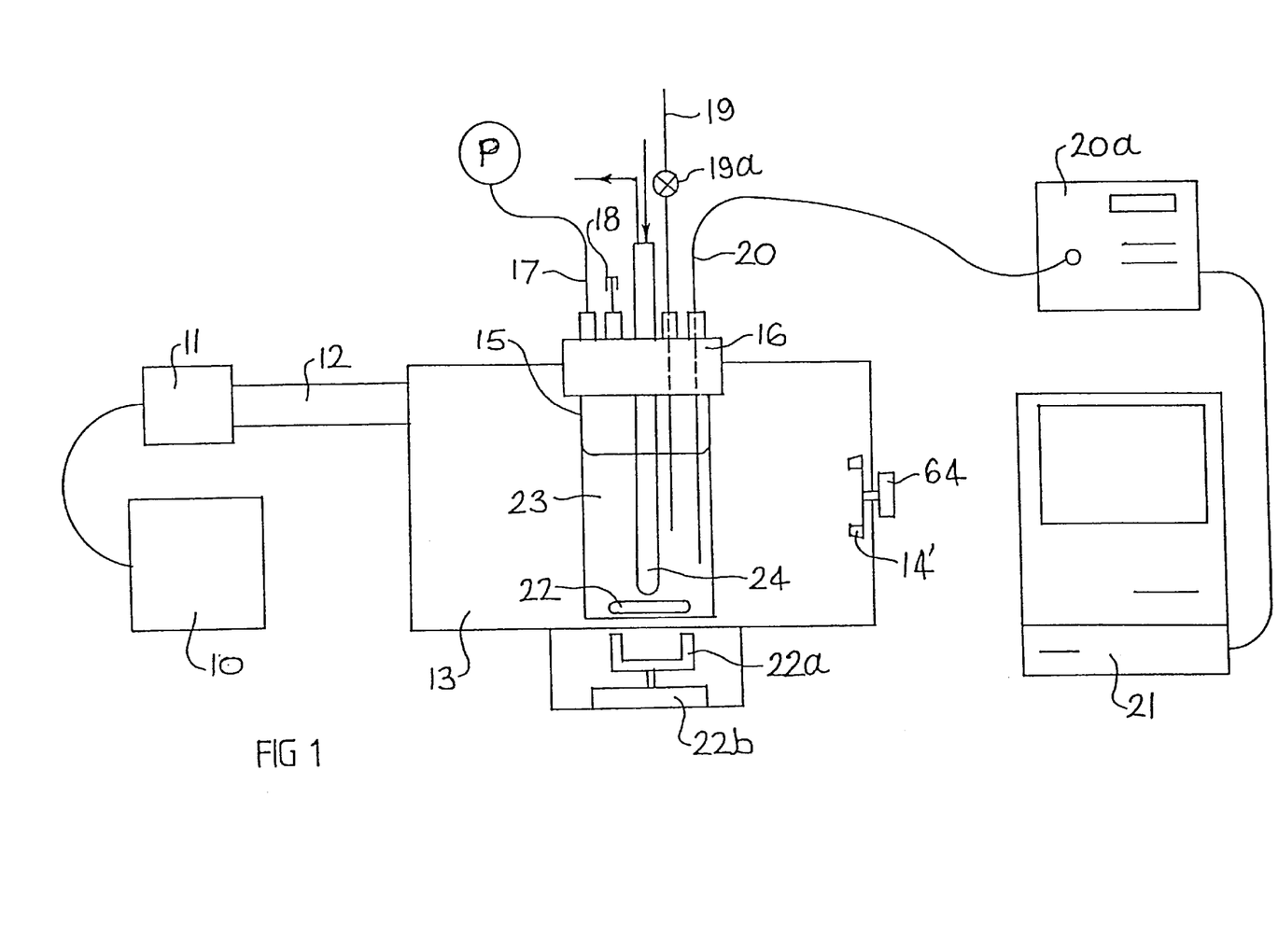
FIG. 1 is a schematic diagram of apparatus embodying the invention.
Figure 2:
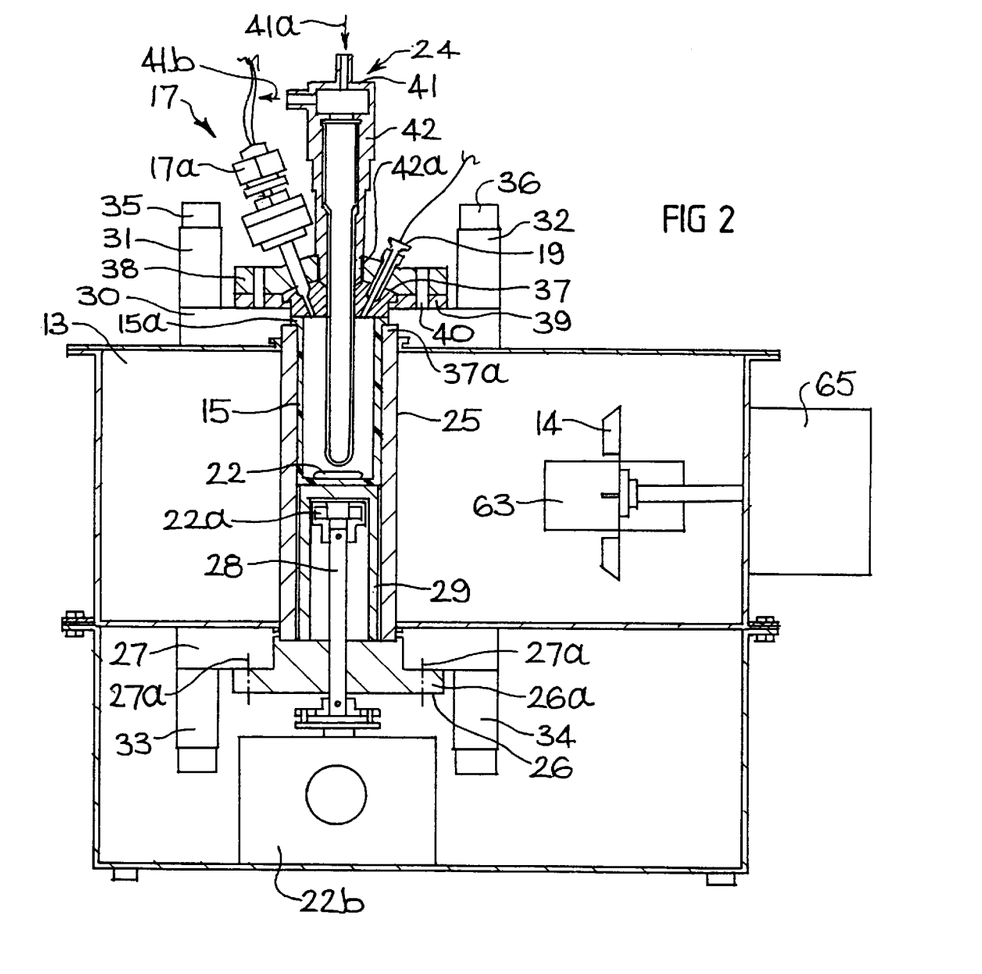
FIG. 2 illustrates a reaction vessel according to the invention within a microwave cavity.

An arrangement of apparatus that embodies the invention is shown schematically in FIG. 1. The illustrated apparatus includes a variable power generator 10 for supplying variable power to a magnetron 11. This arrangement allows the magnetron to run at a chosen power setting or for the magnetron power to be varied, as in the case of temperature feedback control. The power supply may be a "National Power Generator Model NL 10320" and the magnetron a 1.2 kW, 2450 MHz unit. Microwaves generated by a magnetron 11 are conveyed to a microwave cavity enclosure 13 via a waveguide 12. Enclosure 13 may include a load matching device 14' connected to an adjustment knob 64 (or a mode stirrer 14 connected to an electric motor 65 as shown in FIG. 2).

Microwave enclosure 13 contains a reaction vessel 15 having a cover 16 which carries various monitoring and control means. These monitoring and control means (which are to be described in detail below) include a pressure measurement arrangement 17, a safety valve assembly 18, a sampling facility 19 and a temperature measurement arrangement 20. Both the pressure and temperature measurement arrangements may be linked to a computer 21 for data logging (note that FIG. 1 does not illustrate the pressure measurement arrangement as being linked to the computer 21). The invention also encompasses computer control of the power supply based on feedback temperature and/or pressure measurements. That is, the apparatus may include control facilities which allow pre-selection of a temperature and/or pressure value and variation of the input energy dependent upon such selected value(s).

Reaction vessel 15 may include a stirrer bar 22 for minimising thermal gradients within a reaction mixture 23. Bar 22 is magnetically driven by a magnet 22a which is rotated by motor 22b. Suitable such magnetic stirrers are disclosed in International Patent Application No. PCT/AU92/00454 (International Publication No. WO 93/05345). Magnet 22a, if it is located within the microwave field, for example as shown in FIG. 2, should be shielded from the microwave field.

Cover 16 of reaction vessel 15 also supports a heat exchange means 24 which extends through the cover and into vessel 15 for immersion within a reaction mixture 23.

FIG. 2 is a sectional view showing details of the reaction vessel and microwave cavity construction. It is necessary that the construction be such as to withstand the high pressures that can develop within the sealed reaction vessel. As illustrated in FIG. 2, the microwave enclosure 13 includes an alumina cylinder 25 extending between apertures in its top and bottom walls. The bottom end of cylinder 25 is supported on a cover 26 which fits within an aperture in plate 27 that covers the bottom wall of enclosure 13 adjacent to and surrounding cylinder 25. Cover 26 is fixed to plate 27 (for example by screws passing through a peripheral flange 26a of cover 26 that overlaps plate 27. Such screws are not illustrated, but would be located at positions referenced 27a). A shaft 28, for example of PTFE, passes through cover 26 and couples an electric motor 22b to a magnet 22a for driving a stirrer bar 22 within reaction vessel 15. Cover 26 also supports an alumina pedestal 29 for supporting the bottom of the reaction vessel 15.

The top wall of enclosure 13 adjacent to and surrounding alumina cylinder 25 is covered by a plate 30 similar to the bottom plate 27. Cross beams 31 and 32, which extend across plate 30, and cross beams 33 and 34, which extend across plate 27, extend beyond the opposite side walls of enclosure 13 such that they can be bolted together by long bolts on either side of enclosure 13. Thus beams 31 and 33 are connected by bolts 35 and beams 32 and 34 are connected by bolts 36 on either side of the enclosure. It will be appreciated that the plates 27 and 30, and connected cross beams 31–33, 32–34 provide a strengthened structure in the vicinity of the reaction vessel both to assist in withstanding the high pressures within reaction vessel 15 and to contain any explosion which may occur. In this connection, the central aperture of plate 30 provided for the reaction vessel 15 includes a recess 37a in which the top rim of alumina cylinder 25 is seated.

Reaction vessel 15 is supported on a pedestal 29 within alumina cylinder 25. The outer diameter of vessel 15 is only slightly less than the inner diameter of cylinder 25 and the wall thickness of cylinder 25 must be of sufficient thickness to provide adequate support for vessel 15 to withstand the high pressures developed within the vessel during a chemical reaction. Alternatively, an arrangement for supplying pressure from an external source to the exterior surface of vessel 15 equal to the internal pressure developed therein could be used in place of a structural member such as alumina cylinder 25.

Vessel 15 includes a lip 15a that seats on the top rim surface of cylinder 25. Vessel 15 should preferably be constructed of an inert material, for example polyether ether ketone (PEEK).

Figure 2A:
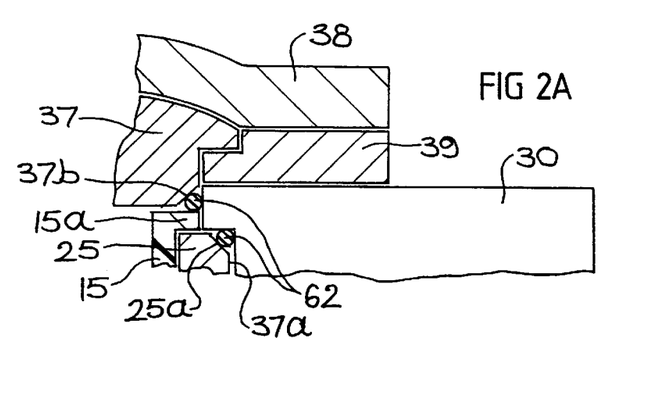
FIG. 2A shows a portion of the FIG. 2 apparatus in detail.

Cover 16 of the reaction vessel 15 comprises a dome 37 of inert material, for example PEEK, held captive between two plates 38 and 39 which are attached together by screws 40. Dome 37 is seated within an aperture in bottom plate 39 and top plate 38 extends over both plate 39 and dome 37, thus plate 38 includes a central dome shaped section corresponding to the shape of dome 37. As illustrated in FIG. 2A, a bottom surface of dome 37 extends over the upper surface of the rim 15a of vessel 15 and an O-ring seal 62 is interposed between the two within a space created by a chamfer 37b on PEEK dome 37. This structure ensures that the containment surfaces of the reaction vessel are comprised of inert material. Also, as shown in FIG. 2A, an O-ring seal 62 is interposed between alumina cylinder 25 and plate 30 within the recess 37a. A chamfer 25a at the outer rim of cylinder 25 allows space for the seal 62.

The cover assembly 16 may be fixed in place by removable screws (not shown) passing through plates 38 and 39 into plate 30. It will be appreciated that the dome 37 and plates 38 and 39 comprising cover 16 must be of sufficient strength to withstand the high pressures that will be generated within vessel 15.

The heat exchange means 24 carried by cover 16, as illustrated in FIG. 2, comprises a "cold-finger" structure. This consists of a tube 41, for example, of quartz or other suitable inert material, that passes through dome 37 and extends into reaction vessel 15 such that it will be immersed within a reaction mixture 23. The lower end of the tube 41 is closed and the upper portion is carried within a tubular mounting 42 having a lower portion 42a that is screwed into plate 38 of cover 16. Quartz tube 41 contains a tube for carrying a heat exchange medium (for example cold water) from an inlet end 41a to the closed lower end of tube 41, from which end the medium rises within tube 41 (that is within the annular passage between the inlet tube and the quartz finger 41) to exit from the heat exchange means at 41b.

Instead of the illustrated cold-finger type of heat exchange means, the invention could utilize other structures such as, for example, a coiled heat exchanger. This would have the advantage of providing a greater surface area for cooling, but concomitantly would be more intrusive; that is it would be more difficult to clean and thus would carry a higher risk of contamination of a reaction mixture within vessel 15 when subsequently used. Generally, the cold-finger type of heat exchanger is preferred to other types. Also, materials other than quartz may be used for the heat exchanger, for example, a metal such as stainless steel may be used in some circumstances. It is important that the heat exchange means be constructed of a material that will not affect or contaminate a chemical reaction within vessel 15.

In addition to the heat exchange means 24, cover 16 also contains a pressure measurement arrangement 17, a safety valve assembly 18, a sampling facility 19, and a temperature measurement arrangement 20. Note that the sectional view shown in FIG. 2 does not show the safety valve 18 or temperature measurement arrangement 20.

Figure 3A:
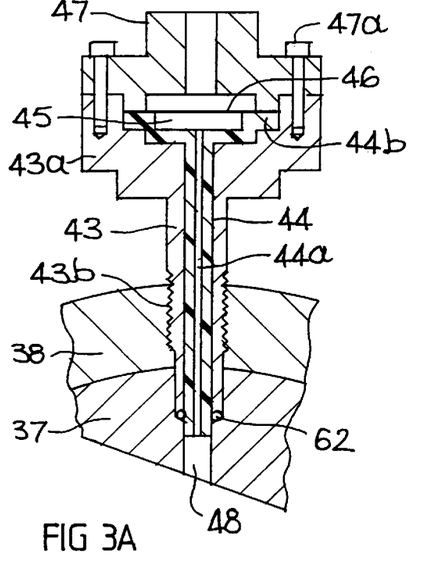
FIGS. 3A, 3B, 3C & 3D show details of fittings of the reaction vessel of FIG. 2.

The pressure measurement arrangement 17 is illustrated in FIG. 3A and comprises a tubular fitting 43 screwed into cover plate 38 at 43b. Tubular fitting 43 contains a liner 44, for example of PEEK, having a central passage 44a in communication with the vessel 15 via passage 48 in PEEK dome 37. Fitting 43 includes an enlarged head section 43a within which is seated an enlarged head portion 44b of liner 44. The enlarged head portion 44b of liner 44 defines a chamber 45 communicating with passage 44a. One wall of chamber 45 is defined by a diaphragm 46, for example, of an inert material such as fluoroethylene polymer mounted between fitting 43 and another fitting 47, which is attached to head section 43a of fitting 43 by screws 47a. Fitting 47 is adapted to mount a pressure transducer 17a (which is shown in FIG. 2 but not FIG. 3A). The cavity between the diaphragm 46 and pressure transducer 17a is filled with a liquid such as water.

It will be appreciated from FIG. 3A that all of the containment surfaces for the vessel contents associated with the pressure measurement arrangement are comprised of inert material. Sensing of the pressure that is developed within the vessel 15 is via passages 48 and 44a, chamber 45 and diaphragm 46 for conversion via transducer 17a.

Figure 3B:
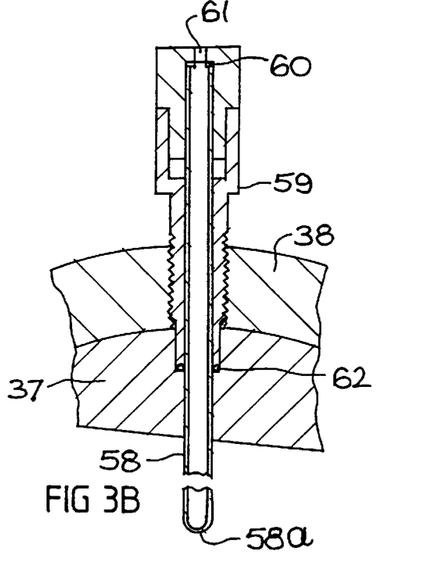

A temperature measurement arrangement 20 for cover 16 is illustrated in FIG. 3B. This comprises a small diameter tube 58, for example of quartz, having a sealed end 58a located within reaction vessel 15. Quartz tube 58 passes through and is supported by a tubular fitting 59 that is screwed into plate 38 of cover 16. Tube 58 is held within fitting 59 by a rubber seat 60 received within an outer end of fitting 59. Rubber seat 60 includes a small aperture 61 opening into the interior of tube 58 for passage of an optical fibre (not shown in FIG. 3B) of a fibre optic thermometer.

The optical fibre extends into the reaction vessel 15 within tube 58 and includes a heat sensitive phosphor tip for temperature sensing. The other end of the fibre is connected to an analyzer/display unit 20a (see FIG. 1) which in turn may be linked to a computer 21. A Luxtron Model 755 Multichanel Fluoroptic Thermometer is suitable for use in the invention. Other types of thermometer, however, which are suitable for location within a microwave field such as an infrared sensing arrangement, sheathed thermocouple or gas thermometer, may be used in the invention.

Figure 3C:
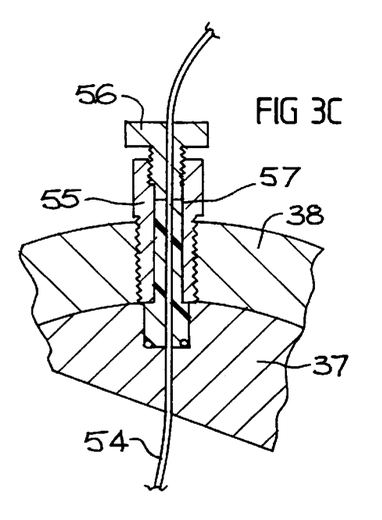

FIG. 3C illustrates a sampling facility 19 for the reaction vessel 15. This facility comprises a small diameter tube 54 (having an outside diameter of, for example, about 1.6 mm) of inert material, for example of PEEK, passing through a tubular fitting 55 screwed into plate 38. One end of a liner 57 of inert material, for example PEEK, is seated within a recess within dome 37 and a nut 56, which is screwed into the outer end of fitting 55, bears upon the other end of the liner 57 to ensure a pressure tight fitting for the liner within the dome 37. PEEK tube 54 will extend into a reaction mixture within vessel 15 (see FIG. 1). The outer portion of tube 54 is sealed by a valve (see 19a in FIG. 1).

The sampling facility 19 allows some of a reaction mixture to be withdrawn from vessel 15 by opening valve 19a while the mixture is being irradiated by microwaves and a chemical reaction is underway. Alternatively it allows a reactant or solvent to be added to the mixture during a reaction. Such an addition of a reactant or solvent will require pressure to be applied to tube 54 higher than the pressure within reaction vessel 15 in order to force the additive into the vessel. Sampling facility 19 may also be used as an inert gas inlet. Arrangements for achieving this would be well known by persons skilled in the art and consequently are not described in detail herein.

Cover 16 may incorporate more than one sampling facility 19. For example, when two such facilities are included it is possible, whilst a chemical reaction is underway within vessel 15, to add a reactant or solvent to the reaction mixture via one sampling tube and to extract reaction products via the other sampling tube.

Figure 3D:
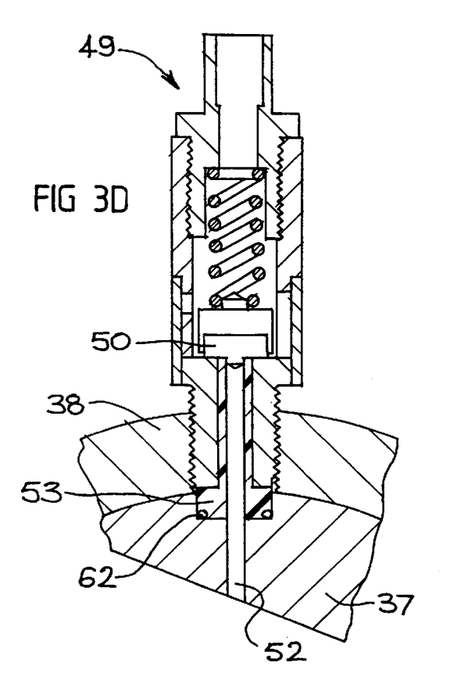

A safety valve arrangement is illustrated in FIG. 3D. This is a standard type of arrangement comprising an adjustable spring biassing arrangement 49 acting on a valve seat 50, the opposite surface of which is in communication with the high pressure region via a passage 52 through dome 37. An important aspect of the arrangement is that all of the containment surfaces be comprised of inert material. Thus, as illustrated in FIG. 3D, the arrangement includes a liner 53 of inert material (for example PEEK) extending between the dome 37 and valve seat 50. The valve seat 50 is also made of inert material, for example, PTFE.

Given that high pressures will be developed within the reaction vessel 15 during a chemical reaction, it is necessary for the components of and fittings on the reaction vessel 15 and cover 16 to be effectively sealed in addition to being of sufficient strength to withstand such pressures. As illustrated in FIGS. 2 and 3, such sealing can be effected by the use of O-rings 62, which are made of a suitable inert material. Generally, O-rings 62 should be used to seal between the vessel 15 and dome 37 of cover 16, and between dome 37, the screw fittings and inserts within cover 16. Furthermore the high temperatures and pressures developed within the reaction vessel increase the risk of contamination of a reaction from the materials the reactants may contact. Consequently, as is mentioned above, all such materials should be non-contaminating for any particular reaction being conducted using the apparatus. Generally, all components which reactants may contact should be made from inert materials such as, for example, PEEK, quartz or PTFE. Other components, such as cover 26, plates 27 and 30, and the cover components (plates 38 and 39, fittings 43, 55, 59 etc.) may be made of stainless steel.

Referring again to FIG. 2, the waveguide aperture into microwave enclosure 13 is shown at 63 and a mode stirrer for the cavity is illustrated at 14. Mode stirrer 14 may be continuously driven in known manner by a motor 65. Alternatively it may be connected to a hand adjustable knob (e.g. knob 64 shown in FIG. 1) for setting at a particular angle as determined by, for example, measurement of the input and reflected microwave power within waveguide 12. That is, waveguide 12 may include devices with associated meters for measuring the input and reflected microwave power to enable adjustment of the mode stirrer 14 by knob 64 to a position wherein the input power is maximised and the reflected power minimised.

In the embodiment illustrated in FIG. 2, the dimensions of cavity 13 are: height 175 mm, width 200 mm and length 400 mm. Alumina cylinder 25 has an o.d. of 70 mm, i.d. of 50 mm and length 200 mm. Reactor vessel 15 has a nominal capacity of 100 ml with the dimensions: o.d. 50 mm, i.d. 44 mm and length 103 mm. Cover 16 has an o.d. of 130 mm, thickness of 15 mm and an internal radius of 65 mm for the domed portion. Dimensions for the cold-finger 41 are 15 mm o.d., 1.5 mm wall thickness and 160 mm length for the finger portion and 20 mm o.d. and 60 mm length for the head portion. With this embodiment, temperatures of 250° C. and pressures of 10,000 kPa (100 Atmos.) have been achieved within vessel 15. It is to be realized, however, that the invention is not limited by the above stated sizes or operating parameters, although there will clearly be practical limits to the capacity of the reaction vessel and the maximum temperature and pressure rating of apparatus according to the invention as determined by the materials used and safety factors.

Figure 4:
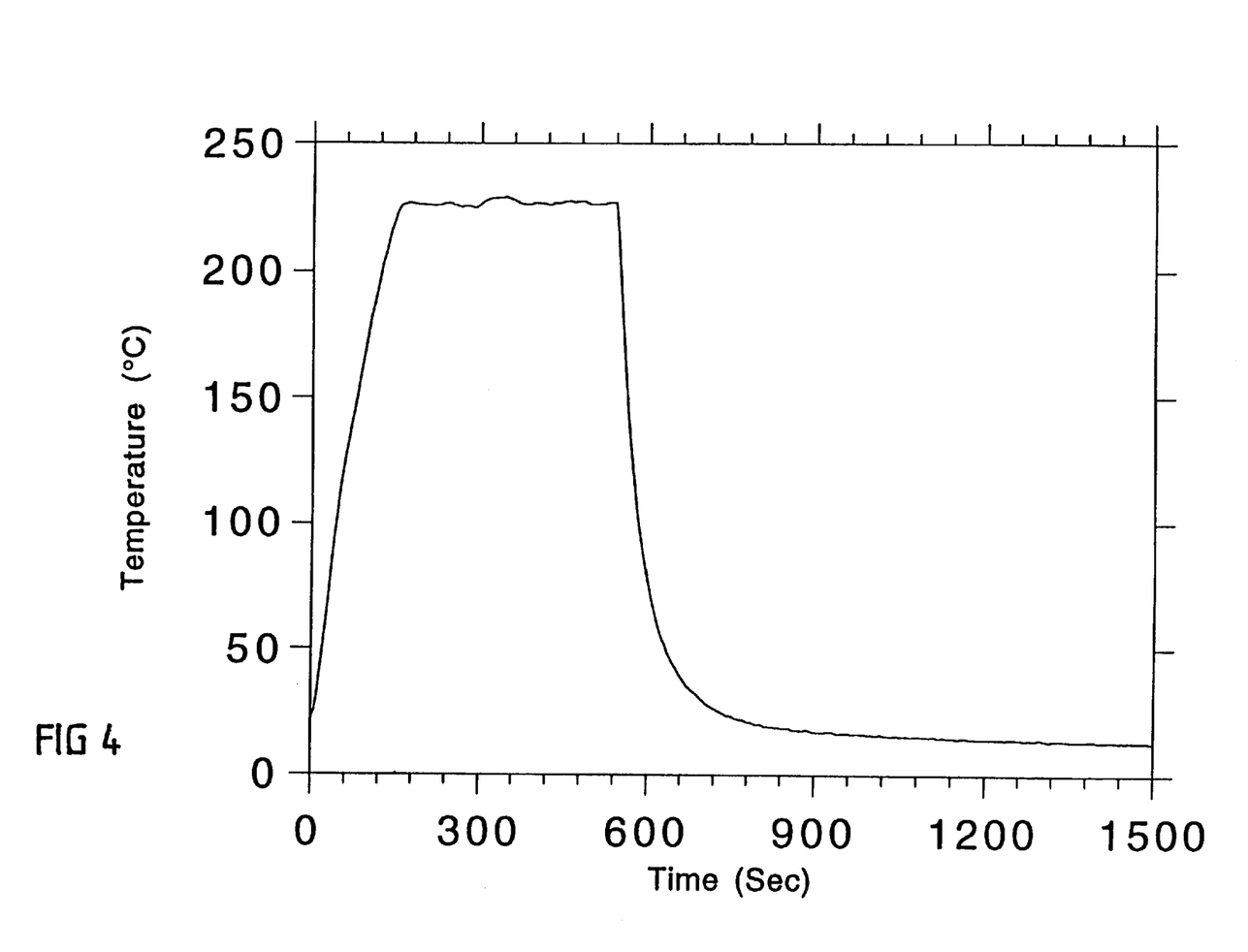
FIG. 4 is a graph illustrating the heating and cooling capability of the invention.

The graph in FIG. 4 illustrates the heating and cooling capability of a batch reactor according to the FIG. 2 embodiment. This graph shows the vessel contents (water) being rapidly heated to a temperature of 230° C. in about 2½ minutes, held at this temperature for about 6½ minutes, and then rapidly cooled to about 30° C. (i.e. a temperature decrease of about 200° C.) in about 2 minutes by passage of a coolant through the cold-finger heat exchanger. In addition to cooling the vessel contents after a reaction, the heat exchange means may also be used to preheat the vessel contents. Such a preheating step is particularly useful for substances which are not good absorbers of microwave energy until heated.

Another mode of use for the cold-finger heat exchanger, particularly with substances that become good absorbers of microwave energy only when heated, is to fill the heat exchanger with a substance such as water which is a good absorber of microwave energy at ambient temperature, assemble the apparatus such that the (eg water) filled heat exchanger and substance(s) for reaction are contained in vessel 15, and irradiate the assembly with microwaves. In this mode of use, the substance within the heat exchanger is first heated and this in turn conductively and convectively heats the substance(s) for reaction within the vessel such that it (or they) become microwave absorbent sufficient to be heated directly by the microwaves. Continued heating of the substance(s) within vessel 15 by the microwaves then causes a chemical reaction within that or those substances.

In any of the above described modes of use, the cold-finger heat exchange means may be emptied of its contents by a syphon means or by pressure means for "blowing-out" the contents.

Typically, a reaction carried out on a 100 mL scale at 200° C. for 5 minutes in a reactor according to the invention may be worked up after a total time of only 10 minutes, the heating up and cooling down processes each requiring only ca. 2.5 minutes.

To exemplify the utility of the invention, examples of reactions using apparatus such as shown in FIG. 2 are now described.

EXAMPLE 1

Use of Cold-Finger (41) for cooling
Preparation of 2-Allylphenol

A mixture of allyl phenyl ether (2.0 g) and water (60 mL) was added to a PEEK vessel equipped with a magnetic stirrer bar. The vessel was placed into the reactor, and the cover sealed. The mixture was heated to 242° C. (pressure 3.3 MPa) within 10 min and held at this temperature for 10 min, then rapidly cooled to 50° C. using the cold-finger. The resulting mixture was extracted with diethyl ether (3×50 mL). The organic extract was dried ($MgSO_4$) and concentrated to afford 2-allylphenol (1.7 g) in 87% purity as determined by GC/MS and $^1$H NMR spectroscopy. GC/MS: m/z (rel.int. %) 134($M^+$, 100), 133(41), 119(38), 115(41), 107(25), 105(30), 91(63), 89(11), 79(29), 78(27), 77(55), 66(11), 65(15), 63(18), 55(11), 53(16), 52(14), 51(38), 50(20).

EXAMPLE 2

Use of Cold-Finger (41) for cooling
Saccharification of Lupin Biomass

A suspension of dried Lupin hull (500 μm particle size, 10 g, containing 52% cellulose by mass) in 1% aqueous $H_2SO_4$ (100 mL) was heated under microwave conditions with stirring. The temperature was raised from 30° C. to 215° C. in 120 seconds, maintained for 30 seconds (pressure ca, 2 MPa), then rapidly decreased by means of the cold-finger to 50° C. The time spent above 200° C. was 1 minute. The conversion of cellulose to glucose was 39%.

EXAMPLE 3

Use of Cold-Finger (41) for cooling
Isomerization of Carvone.

A mixture of p-toluenesulfonic acid (1.4 g) and carvone (11.3 g) in chlorobenzene/1,4-dioxane (4:1 by volume; 75 mL) was heated at 180° C. for 35 min, then rapidly cooled using the cold-finger, and extracted with 10% NaOH solution (3×100 mL). The combined aqueous extract was washed with $CH_2Cl_2$ (2×100 mL), neutralized by dropwise addition of conc $H_2SO_4$, and extracted with $CH_2Cl_2$ (3×100 mL). The organic extract was washed with sat $NaHCO_3$ (100 mL), dried with $MgSO_4$, and concentrated in vacuo to give carvacrol (9.6 g; 85%).

Examples of the Willgerodt Reaction.

EXAMPLE 4

Preparation of Phenylacetamide from Acetophenone

To a suspension of sulfur (15 g, 58.4 mmol) in pyridine (15 mL, 14.67 g, 185.5 mmol) and aqueous ammonia (28%; 20 mL) was added acetophenone (10 g, 83.3 mmol). The stirred mixture was heated rapidly to 185° C., held at this temperature for 10 min, then rapidly cooled using the cold-finger. Concentration (reduced pressure) afforded a solid (32 g) which was suspended in ether (80 mL) then filtered, and the solid collected, washed with ether (2×10 mL), then suspended in boiling water (ca. 1 L) and filtered. The filtrate obtained was continuously extracted with dichloromethane (500 mL) and the organic phase evaporated. The residue was recrystallised from dichloromethane (decolourising charcoal) and dried (vacuum/$P_2O_5$) to afford the acetamide as colourless flakes, m.p. 157–158° C. (8.1 g, 72%).

$v_{max}$ 3364 m, 3192 m, 1640 s, 1498 w, 1456 w, 1418 m, 1290 m, 1204 w, 1184 w, 1156 w, 1136 w, 1136 w, 1074 w, 746 m, 700 m, 583 w, 534 w, 474 w $cm^{-1}$.

$^1H$ n.m.r. ($d_6$ DMSO): δ 3.37, s; 6.91, bs; 7.1–7.35, m; 7.48, bs.

$^{13}C$ n,m,r, ($d_6$ DMSO): δ 42.22, 126.14, 128.03, 128.95, 136.39, 172.16.

Mass spectrum (CI): m/z 136(M+1,100%), 92(17), 91(17).

EXAMPLE 5

Preparation of Phenylacetamide from Styrene

A mixture of sulfur (15 g, 58.4 mmol), pyridine (15 mL, 14.67 g, 185.5 mmol), aqueous ammonia (28%; 20 mL), styrene (8.66 g, 83.3 mmol) and 4-t-butylcatechol (0.23 g, 1.69 mmol) was heated to 170° C. for 10 minutes then rapidly cooled using the cold-finger. Phenylacetamide was obtained upon workup (5.7 g, 51%). No impurities were detected in the $^1H$ n.m.r. or $^{13}C$ n.m.r. spectra.

EXAMPLE 6

Preparation of 4'-Hydroxyphenylacetamide

A mixture of sulfur (15 g, 58.4 mmol), i-propanol (15 mL, 11.78 g, 196 mmol), aqueous ammonia (28%; 20 mL) and 4'-hydroxyacetophenone (11.30 g, 83.1 mmol) was heated to 210° C. for 20 minutes then rapidly cooled using the cold-finger, and the resultant mixture concentrated under reduced pressure. The residue was triturated with ether (3×50 mL) and the solid obtained triturated with boiling water (1×500 mL, 2×250 mL). The combined aqueous phase was evaporated and the residue was recrystallised from water (decolourising charcoal). The crystals were collected by filtration, washed with cold water (20 mL), ether (20 mL), then dried (vacuum/$P_2O_5$) to afford 4'-hydroxyphenylacetamide as a yellow powder, m.p. 171–173° C. (7.35 g, 59%).

$v_{max}$ (KBr wafer) 3700–2200 bs, 1635 s, 1510 m, 1430 s, 1360 m, 1310 w, 1290 m, 1230 s, 1200 m, 1175 m, 1115 m, 1100 m, 1015 w, 925 w, 885 m, 855 m, 820 m, 795 s, 670 s, 565 w, 525 m, 495 w $cm^{-1}$.

$^1H$ n.m.r. ($d_6$ DMSO): δ 3.27, s; 6.71, m; 6.85, bs; 7.08, m; 7.39, bs; 9.26, bs.

$^{13}C$ n.m.r. ($d_6$ DMSO): δ 41.44, 114.93, 126.62, 129.94, 155.81, 172.86.

Mass spectrum (CI): m/z 152(M+1, 100%), 135(9), 134(5), 121(6), 107(45).

EXAMPLE 7

Synthesis of 4'-Hydroxyphenylacetamide

A mixture of sulfur (15 g, 58.4 mmol), i-propanol (15 mL, 11.78 g, 196 mmol), aqueous ammonia (28%; 20 mL) and 4'-acetoxyacetophenone (14.83 g, 83.3 mmol) was heated to 210° C. for 20 min then rapidly cooled using the cold-finger. Workup and recrystallisation afforded 4'-hydroxyphenylacetamide (7.60 g, 61%).

EXAMPLE 8

Preparation of 4'-Methoxyphenylacetamide

A mixture of sulfur (15 g, 58.4 mmol), i-propanol (15 mL, 11.78 g, 196 mmol), aqueous ammonia (28%; 20 mL) and 4'-methoxyacetophenone (12.50 g, 83.3 mmol) was heated to 210° C. for 20 min then rapidly cooled using the cold-finger. The cooled reaction mixture was concentrated and the residual semi-solid was triturated with ether (3×30 mL). Recrystallisation of the remaining solid from water (decolourising charcoal) afforded 4'-methoxyphenylacetamide as colourless plates which were dried under reduced pressure (8.5 g, 62%).

$^1H$ n.m.r. ($d_6$ DMSO): δ 3.31, s; 3.74, s; 6.85, m; 7.19, m; 7.43.

$^{13}C$ n.m.r. ($d_6$ DMSO): δ 41.28, 54.89, 113.49, 128.34, 129.94, 157.76, 172.62.

Mass spectrum (CI): m/z 166(M+1, 100%), 151(5), 149(6).

EXAMPLE 9

Preparation of 4'-Ethoxyphenylacetamide

A mixture of sulfur (15 g, 58.4 mmol), pyridine (15 mL), aqueous ammonia (28%; 20 mL) and 4'-ethoxyacetophenone (13.65 g, 83.3 mmol) was heated to 190° C. for 20 minutes then rapidly cooled using the cold-finger. The resultant mixture was concentrated and the residual semi-solid was triturated with ether (3×30 mL). The residual solid was then suspended in boiling water (5×300 mL) and filtered. The combined aqueous phases were then continuously extracted with dichloromethane. The residue obtained after removal of the solvent was then recrystallised from ethanol (decolourising charcoal) to give 4'-ethoxyphenylacetamide (9.2 g, 62%).

$^1H$ n.m.r. ($d_6$ DMSO): δ 1.36, t; 3.32, s; 4.02, q; 6.88, m; 7.18, m; 7.45.

$^{13}C$ n.m.r. ($d_6$ DMSO): δ 14.68, 41.62, 62.89, 114.08, 128.31, 130.01, 167.46, 172.64.

Mass spectrum (CI): m/z 166(M+1, 100%), 151(5), 149(6).

EXAMPLE 10

Use of a Sampling Facility (19)

Preparation of (2-methoxyethyl)benzene

A mixture of (2-bromoethyl)benzene (2.0 g) and methanol (60 mL) in a PEEK vessel equipped with a magnetic stirrer bar was placed into the reactor, and the cover sealed. The mixture was stirred and heated to 149° C. (1.08 MPa) within 10 min and held at this temperature for 2 hours. Samples were withdrawn periodically and analysed. The mixture was then cooled. After 1 hour the conversion to (2-methoxyethyl)benzene was 50% increasing to 80% after 2 hours. GC/MS: m/z (rel.int. %) 136(M $^+$, 13), 104(8), 91(28), 77(6), 65(11), 63(4), 51(9), 50(4), 45(100). $^1$H NMR, (CDCl$_3$; 200 MHz): δ7.23, m, 5H, Ar; 3.6, t, 2H, —CH$_2$—O—CH$_3$; 3.4, s, 3H, —O —CH$_3$; 2.9, t, 2H, Ar—CH$_2$—.

EXAMPLE 11 adding and subtracting substances during a reaction (eg via sampling facilities 19)
Preparation of 6-Bromohex-1-ene 1,6-Dibromohexane (30 mL, 48 g) was placed in a PTFE reactor vessel along with a magnetic stirrer bar. The reactor was set up with a 3 mm O.D. outlet tube connected to the cover assembly. The dibromide was heated to 150° C. and hexamethylphosphorous triamide (HMPTA; ca. 3 mL) was added through a second tube attached to the cover assembly, by means of a syringe. The vessel contents were then heated to 200° C. and HMPTA (42 mL) was added dropwise through the syringe. The crude product distilled through the exit tube and was collected in chilled flasks, then redistilled to give 6-bromohex-1-ene (15.6 g, 49%). $^1$H NMR (CDCl$_3$; 200 MHz): δ1.56, m, 2H, CH$_2$; 1.85, m, 2H, CH$_2$; 2.10, m, 2H, CH$_2$; 3.41, t, J=7 Hz, 2H, CH$_2$Br; 4.85–5.10, m, 2H, =CH$_2$; 5.80, m, 1H, =CH, in agreement with that reported by Kenneth J. Shea and Jang-Seob Kim in "Influence of Strain on Chemical Reactivity, Relative Reactivity of Torsionally Distorted Double Bonds in MCPBA Epoxidations" Journal of The American Chemical Society, Vol.114 No.8, 1992, pages 3044–3051.

EXAMPLE 12

Use of Cold-Finger as a Preheater
Dehydration of 4-t-butylcyclohexanols.
(a) With liquid in the cold-finger being heated by the applied microwave energy (ie. acting as a susceptor).

The microwave reactor was configured as for the preparation of 6-bromohex-1-ene, with the exception that an atmosphere of nitrogen was maintained in the reaction vessel. The quartz cold-finger was charged with water, and the PTFE reaction vessel was charged with a finely ground mixture of cis- and trans-4-t-butylcyclohexanol (40 g, 256.4 mmol) and potassium pyrosulfate (20 g). Microwave power was then applied to heat the water in the cold-finger to boiling and the reaction temperature then began to rise. The reaction was heated to 175° C. by microwave energy and maintained at this temperature while a two-phase distillate was collected over ca. 10 min. During the distillation, the water in the cold-finger was serving as a "dummy load" absorbing excess input microwave energy, and decreasing the reflected power. The organic layer was separated, washed with water (4×10 mL) then dried (MgSO$_4$). The product (22.3 g) consisted of 4-t-butylcyclohexene (89% by GC analysis) and 3-t-butylcyclohexene (11% by GC analysis). $^{13}$C n.m.r. (CDCl$_3$; 50 MHz): for 4-t-butylcyclohexene δ 23.93, 26.71, 26.78, 27.11, 32.22, 44.11, 126.78, 127.31, for 3-t-butylcyclohexene δ 22.87, 24.43, 25.22, 27.43, 32.67, 45.90, 127.91, 129.25.
(b) With externally preheated liquid flowing through the cold-finger The microwave reactor was configured as for Example 12(a). The vessel was charged with a mixture of cis- and trans-4-t-butylcyclohexanol (40 g) and potassium pyrosulfate (20 g). Hot liquid (150–160° C.) was passed through the cold-finger to preheat the vessel contents to 75° C., and then microwave power was applied. The reaction was heated to 175° C. by microwave energy and maintained at this temperature while a distillate was collected. Workup as for Example 12(a) afforded a liquid (27 g) with 4-t-butylcyclohexene the major component.

EXAMPLE 13

Use of the cold-finger for cooling to control the temperature of a reaction
Oxidation of 4-t-Butylcyclohexanols to 4-t-Butylcyclohexanone A solution of chromium (VI) oxide (10 g, 100 mmol) in acetic acid (50 mL) and water (10 mL) was placed in the microwave reaction vessel. Liquid (–35° C.) was circulated through the cold-finger and when the temperature of the contents of the vessel was ca. –5° C., a solution of 4-t-butylcyclohexanols (9 g, 64.1 mmol) in acetic acid (25 mL) was added. Circulation of cooling fluid was maintained through the cold-finger and the temperature of the reaction was increased to 25° C. by the application of microwave power. The temperature was held in the range 25–28° C. for 1 h, then the cooling flow was turned off and the reaction vessel contents were heated to 110° C. for 15 min, then cooled to 20° C. Methanol (5 mL) and water (20 mL) were then added. Steam distillation of the product was conducted and CH$_2$Cl$_2$ workup of the distillate afforded 4-t-butylcyclohexanone as white crystals. The product showed the following EI/MS (at 70 eV): 154 (M+11%), 98 (54), 83 (21), 69 (16), 57 (100).

For comparison, a solution of 4-t-butylcyclohexanols (4.5 g) in acetic acid (15 mL) was added to a solution of chromium (VI) oxide (5 g) in water (5 mL) and acetic acid (25 mL) at ambient temperature, without cooling. A vigorous, uncontrolled exothermic reaction ensued, and the temperature of the mixture increased to 105° C. within 10 seconds.

It will be appreciated that the invention described herein is susceptible to variations or modifications other than those specifically described and it is to be understood that the invention includes all such variations or modifications which fall within the spirit and scope of the invention as defined in the appended claims.

We claim:

1. A reactor for performing chemical reactions under the influence of microwave radiation comprising a vessel for containing substances for a chemical reaction, a microwave radiation source and means for applying microwave radiation from the source into the vessel, said vessel adapted to withstand high internal pressures generated by said substances during the course of the chemical reaction, said adaptation including the provision of a cover containing means for monitoring vessel contents under the influence of the microwave radiation and wherein the cover also supports a heat exchange means for immersion in the vessel contents.

2. A reactor as claimed in claim 1 wherein the heat exchange means is a cold-finger type of heat exchanger.

3. A reactor as claimed in claim 1 wherein the heat exchange means comprises a heat exchange tube having a closed end.

4. A reactor as claimed in claim 3 wherein said heat exchange tube contains and surrounds a smaller diameter inlet tube which terminates proximate said closed end, said inlet tube provided for conveying a heat-exchange fluid into the heat exchange means, wherein said heat-exchange fluid exits the heat exchange means via an annular passage defined between said inlet tube and the surrounding heat exchange tube.

5. A reactor as claimed in claim 3 wherein said heat exchange tube extends substantially normally from said cover.

6. A reactor as claimed in claim 3 wherein said heat exchange tube includes a coiled portion.

7. A reactor as claimed in claim 1 wherein the means for monitoring the vessel contents include a pressure measuring means.

8. A reactor as claimed in claim 7 wherein the pressure measuring means comprises a fitting that screws into the cover and a pressure transducer mounted on the fitting, wherein the fitting includes a passage for communication of pressure between the interior of said vessel and said transducer.

9. A reactor as claimed in claim 1 wherein the means for monitoring the vessel contents include a temperature measuring means.

10. A reactor as claimed in claim 9 wherein the temperature measuring means comprises a fitting that screws into the cover and which mounts a small diameter tube having a sealed end that is located within the vessel, said small diameter tube containing an optical fibre of a fibre optic thermometer.

11. A reactor as claimed in claim 1 wherein said cover additionally includes a pressure operable safety valve assembly.

12. A reactor as claimed in claim 1 wherein said cover additionally includes sampling means for adding the substances to or subtracting the substances from said vessel during microwave heating.

13. A reactor as claimed in claim 12 wherein said sampling means comprises a fitting that screws into said cover and which mounts a small diameter open ended tube that passes into the vessel, said tube extending from said fitting for connection to a valve means located outside said vessel for sealing the tube.

14. A reactor as claimed in claim 1 2 wherein the cove includes two sampling means, one of said sampling means being for adding a substance to the vessel and the other sampling means for simultaneously extracting reaction products from the vessel during the chemical reaction.

15. A reactor as claimed in claim 1 wherein said vessel is in a microwave cavity, said cover being located outside said cavity.

16. A reactor as claimed in claim 15 wherein said cavity includes structural means for strengthening the cavity in a region of said vessel and said cover.

17. A reactor as claimed in claim 1 wherein said cover additionally includes means for introducing the microwave radiation interiorly of the vessel.

18. A reactor as claimed in claim 1 wherein the adaptation of said vessel to withstand said high internal pressures includes placement of the vessel within a surrounding support means.

19. A reactor as claimed in claim 1 wherein the adaptation of said vessel to withstand said high internal pressures includes means for pressurizing the exterior surface of the vessel.

20. A method for performing a chemical reaction comprising:

(i) charging a vessel, which is adapted to withstand a high pressure and a high temperature, with at least one reactant or a reactant and solvent mixture, wherein the reactant or solvent or a susceptor mixed therewith is an absorber of microwave energy, (ii) applying microwave energy to the vessel for the chemical reaction to occur, and (iii) cooling reaction products while they are still contained in the vessel under pressure via heat exchange means immersed therein.

21. A method as claimed in claim 20 wherein said chemical reaction is a Wiligerodt reaction.

22. A method for performing a chemical reaction comprising:

(i) charging a vessel, which is adapted to withstand a high pressure and a high temperature, with at least one reactant or a reactant and solvent mixture which when heated will react exothermically and wherein the reactant or solvent or a susceptor mixed therewith is an absorber of microwave energy, (ii) applying microwave energy for an exothermic chemical reaction to occur, and (iii) during the reaction, cooling vessel contents while they are contained in the vessel under pressure via a heat exchange means immersed therein.

23. A method for performing a chemical reaction comprising:

(i) charging a vessel, which is adapted to withstand a high pressure and a high temperature, with at least one reactant or a reactant and solvent mixture which is a poor absorber of microwave energy at ambient temperature arid a good absorber of the microwave energy when heated, (ii) immersing a heat exchange means in vessel contents and sealing the vessel, wherein the heat exchange means is charged with a microwave absorbent medium, (iii) applying the microwave energy to the vessel to heat the medium within the heat exchange means and to thus heat the vessel contents, where said contents increasingly absorb microwave energy, and (iv) continuing to apply the microwave energy to the vessel contents for the chemical reaction to occur.

* * * * *